United States Patent
Wendt

(10) Patent No.: US 11,554,037 B2
(45) Date of Patent: Jan. 17, 2023

(54) RESTRAINT ASSEMBLY

(71) Applicant: Lorne Wendt, South Range, WI (US)

(72) Inventor: Lorne Wendt, South Range, WI (US)

(*) Notice: Subject to any disclaimer, the term of this patent is extended or adjusted under 35 U.S.C. 154(b) by 470 days.

(21) Appl. No.: 16/809,896

(22) Filed: Mar. 5, 2020

(65) Prior Publication Data
US 2020/0289305 A1 Sep. 17, 2020

Related U.S. Application Data

(60) Provisional application No. 62/816,494, filed on Mar. 11, 2019.

(51) Int. Cl.
*A61F 5/37* (2006.01)
*A44B 11/00* (2006.01)
*B60R 22/18* (2006.01)

(52) U.S. Cl.
CPC .......... *A61F 5/3776* (2013.01); *A44B 11/005* (2013.01); *B60R 2022/1806* (2013.01)

(58) Field of Classification Search
CPC ................. A61F 5/3776; A44B 11/005; B60R 2022/1806
See application file for complete search history.

(56) References Cited

U.S. PATENT DOCUMENTS

| | | | | |
|---|---|---|---|---|
| 5,159,715 A | * | 11/1992 | Jurga | A63B 71/12 2/2.5 |
| 7,013,497 B1 | * | 3/2006 | Grant | A44B 11/006 2/459 |
| 2002/0038573 A1 | * | 4/2002 | Clark | B60R 22/18 73/862.391 |
| 2007/0151004 A1 | * | 7/2007 | Brassill | A63B 71/12 2/461 |
| 2012/0311769 A1 | * | 12/2012 | Lee | A63B 71/12 2/272 |
| 2019/0047509 A1 | * | 2/2019 | Klubach | B60R 22/18 |

* cited by examiner

*Primary Examiner* — David M Upchurch
(74) *Attorney, Agent, or Firm* — Edwin E. Voigt, II

(57) ABSTRACT

The restraint assembly includes a mounting plate having a vertical slot. The plate covers an opening in a surface which is located to restrain a patient. An adapter buckle has a "T" stop which is releasably coupled to the vertical slot. The buckle includes an arm and a head. The head includes a horizontal slot for releasable receipt of a strap of the patient restraint. The arm includes an angular bend which positions the head relative to the plate during use. A lock may be used to prevent undesired separation of the buckle from the plate.

13 Claims, 2 Drawing Sheets

RESTRAINT ASSEMBLY

CROSS-REFERENCE TO RELATED APPLICATIONS

This application claims the benefit of U.S. Provisional Patent Application Ser. No. 62/816,494 filed on Mar. 11, 2019, the entire contents of which being hereby incorporated by reference in its entirety.

FIELD OF THE INVENTION

This invention relates to anchors for patient restraint devices. One or more restraint assemblies may be incorporated into a medical bed to improve patient safety and reduce risk of injury, while simultaneously improving flexibility and the ease of connection and disconnection of patient restraint devices during use.

BACKGROUND

Patient restraint devices frequently include straps which are used to limit mobility in cases where a patient/individual may pose a danger to themselves or others. The patient restraint devices are used with the utmost concern for patient safety and employ every conceivable feature to avoid causing additional injury to ligature, muscle, bones or other bodily portions or organs of a patient. Patient restraint devices may be used in surgical applications, to limit movement following a medical procedure or in situations where the mobility of a patient/individual is required to be restricted to insure the safety to the patient/individual or to others including medical staff.

A patient restraint devices may be used to maintain a proper bodily position during a medical procedure. Alternatively, a patient may need their arms to be restrained to ensure that tubes and catheters are not removed which are providing critical medicine and fluids. Some restless or confused patients require restraints to prevent the patient from getting out of bed before recovery or reducing the chance of falling and injury. Restraints are also utilized for patients being transported on stretchers to diminish the risk of falling off the stretcher. Patient restraints may also be used in psychiatric settings to prevent patients from harming themselves or others.

In the past, patient restraint devices have been anchored to various locations proximate to a medical bed including the bed rails and adjacent walls. The use of the known anchor locations was frequently problematic and required excessive time to secure an individual into a desired position.

In the past, patient restraint devices have not included components which may be easily and quickly assembled together, in order to provide a desired secure position for a patient/individual. In addition, the known patient restraint devices have not provided the flexibility to be easily disassembled, enabling relocation of a patient/individual to an alternative site or position.

Further, in the past, patient restraint devices have not included a locking feature to reduce risk of inadvertent separation of a patient restraint device from an anchor during use of the patient restraint device.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. § 1.56(a) exists.

All U.S. patents and applications and all other published documents mentioned anywhere in this application are incorporated herein by reference in their entireties.

Without limiting the scope of the invention, a brief description of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided for the purposes of complying with 37 C.F.R. § 1.72.

GENERAL DESCRIPTION OF THE INVENTION

The restraint assembly is generally formed of a mounting plate having a front, a rear, and a vertical slot located centrally with respect to the front, the mounting plate further having a lock opening positioned below the vertical slot; an adapter buckle is releasably coupled to the mounting plate, the adapter buckle having an exterior section and interior section, the exterior section having a head having a horizontal slot and an arm extending downwardly from the head, the arm having an angular bend, the angular bend having an angle of 145°, the interior section having a portion of the arm below the angular bend, and a "T" shaped stop integral to the arm opposite to the head, wherein the stop is placed in a first pre-coupled position where the stop is in a vertical orientation exterior to the vertical slot, the stop being inserted through the vertical slot in a second pre-coupled position, and the exterior section and interior section being rotated 90° to position the angular bend upwardly to dispose the head proximate to an upper edge of the mounting plate in the coupled position, wherein the stop extends horizontally outwardly in opposite directions relative to the vertical slot to the rear; and a lock assembly having a lock cylinder and a keeper is disposed through the lock opening, positioning the keeper to the rear, the keeper having a locked position and an unlocked position wherein in the locked position the keeper is in a upward orientation engaging the stop, and in the unlocked position the keeper is in a horizontal orientation disengaged from the stop.

In one embodiment, the mounting plate has a plurality of apertures, each of the apertures receiving a fastener where the fasteners are nuts and bolts or screws.

In another embodiment, the mounting plate has a shape being selected from the group consisting of rectangular, square, circular, oval, pentagonal, hexagonal and octagonal.

In another embodiment, the mounting plate and the adapter buckle are formed of stainless steel.

In another embodiment, the mounting plate includes a rear cover, the rear cover being positioned over the stop and engaged to the rear, the rear cover being square or rectangular in shape.

In another embodiment, the head is adjacent to the front of the mounting plate in the coupled position and the horizontal slot is positioned to receive a restraint strap of a patient restraint device.

In another embodiment, the mounting plate has a height dimension of four inches, a width dimension of four inches, and a thickness dimension of 3/16 inches, the vertical slot has a height dimension of one inch and a width dimension of 1/2 inch and the rear cover is formed of metal, the rear cover having a height dimension of 1½ inches, a width dimension of 2 inches, and a depth dimension of 1 inch.

In another embodiment, the rear cover is attached to the rear of the mounting plate by cover fasteners or by welding.

In an alternative embodiment, a restraint assembly includes a mounting plate having a front, a rear, and a vertical slot located centrally with respect to the front; an adapter buckle releasably coupled to the mounting plate, the adapter buckle having an exterior section and interior section, the exterior section having a head having a horizontal slot and an arm extending downwardly from the head, the arm having an angular bend, the angular bend having an angle of 145°, the interior section having a portion of the arm below the angular bend, and a "T" shaped stop integral to the arm opposite to the head; wherein the stop is placed in a first pre-coupled position where the stop is in a vertical orientation, the stop being inserted through the vertical slot in a second pre-coupled position, and the exterior section and the interior section being rotated 90° to position the angular bend upwardly and to dispose the head proximate to an upper edge of the mounting plate in the coupled position, wherein the stop extends horizontally outwardly in opposite directions relative to the vertical slot to the rear.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described a embodiments of the invention.

DETAILED DESCRIPTION OF THE PREFERRED EMBODIMENTS

Figure 1:
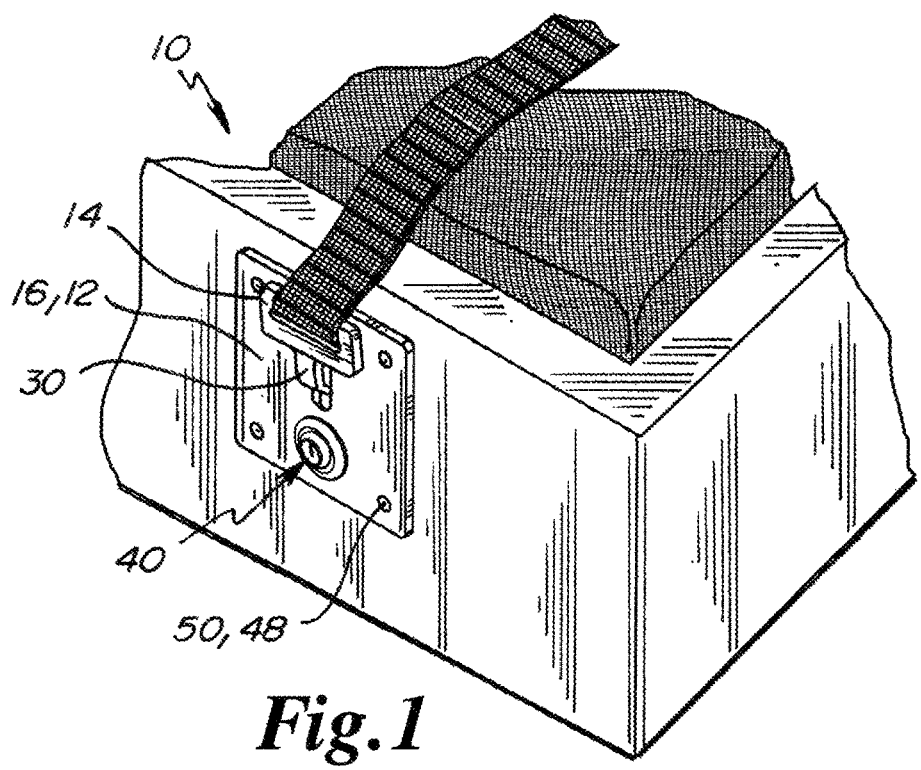
FIG. 1 is an environmental perspective view of the restraint assembly engaged to a bed.
Figure 2:
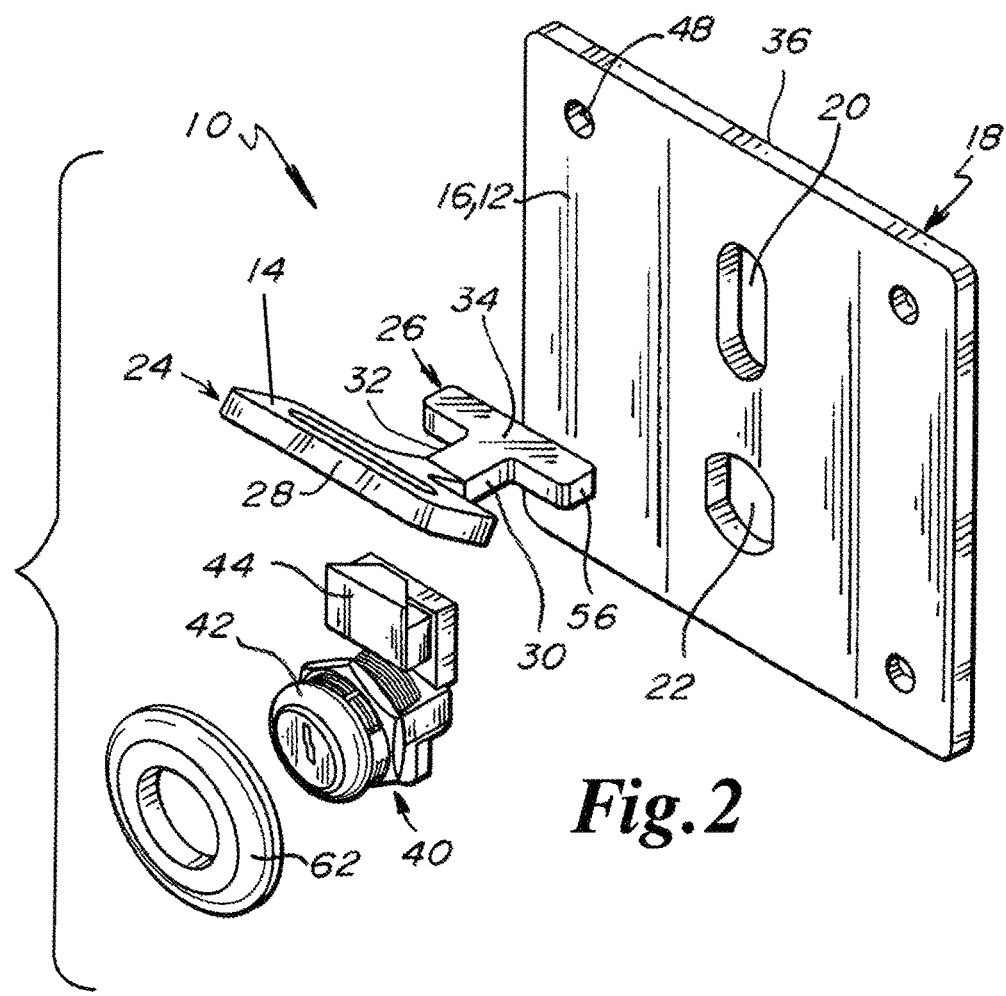
FIG. 2 is a perspective exploded view of the restraint assembly.
Figure 3:
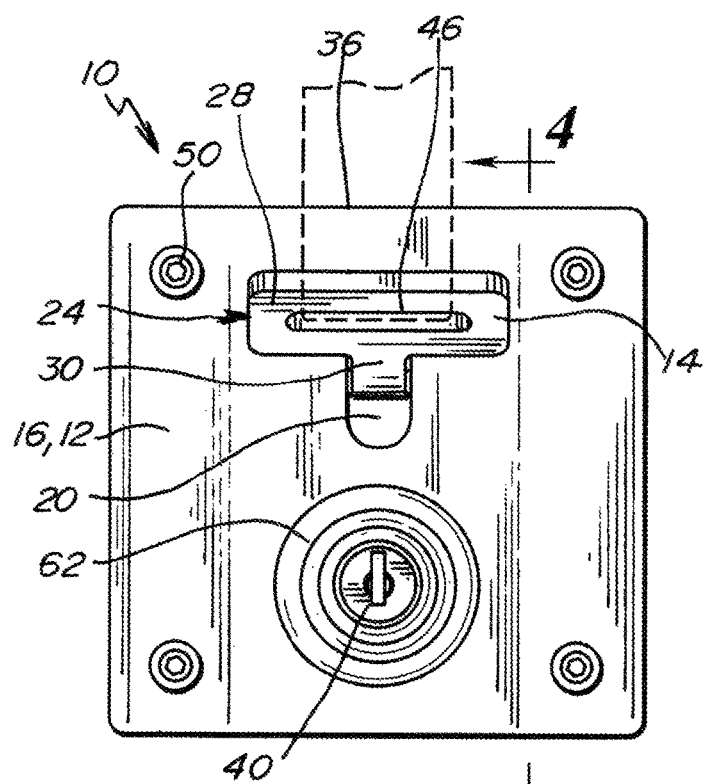
FIG. 3 is a front elevation view of the restraint assembly.

In general, referring to FIGS. 1 through 5, the restraint assembly is identified by reference numeral 10. The restraint assembly 10 is preferably securely attached to a medical bed to assist in the control of a patient to improve the safety to the patient and to care providers.

In general, a circular other shaped opening 54 may be placed into a bedframe at any desired location. In a preferred embodiment each opening 54 will receive one restraint assembly 10. Each opening 54 preferably has a diameter dimension of 3 inches. The size of the opening 54 may be increased or decreased dependent on the size selected for the mounting plate 12 of the restraint assembly 10.

The restraint assembly 10 may be used at a single location and/or at any location proximate to a medical bed. Alternatively, the restraint assembly 10 may be used in pairs or multiple pairs on opposite sides of a medical bed dependent upon the needs of a patient.

In general, a mounting plate 12 is positioned over the opening 54 and is secured to the medical bed frame through the use of one or more fasteners 50, which in some embodiments may be heavy duty bolts and nuts and/or screws. The mounting plate 12 may be formed of stainless steel and may have a height dimension of 4 inches, a width dimension of 4 inches and a thickness dimension of 3/16 inches. In alternative embodiments, the length dimension for the mounting plate 12 may be more or less than 4 inches, the width dimension may be more or less than 4 inches, and the thickness dimension may be more or less than 3/16 inches.

In some embodiments, the mounting plate 12 is square. In other embodiments, the mounting plate 12 may be rectangular, circular, oval, hexagonal, pentagonal, or octagonal, or any other shape as preferred in a particular application.

In at least one embodiment, the mounting plate 12 includes a plurality of apertures 48 where each aperture 48 receives a fastener 50 to secure the mounting plate 12 to the medical bed frame.

In at least one embodiment, the mounting plate 12 includes a front 16, a rear 18, and a vertical slot 20. The vertical slot 20 is preferably centrally located and is oriented vertically relative to the front 16, and passes completely through the front 16 and rear 18. In some embodiments, the vertical slot 20 has a height dimension of 1 inch and a width dimension of ½ inch. In other embodiments, the height dimension for the vertical slot 20 may be more or less than 1 inch, and the width dimension may be more or less than ½ inch. In at least one embodiment, the vertical slot 20 includes an arcuate or rounded edge at the top and/or bottom of the vertical slot 20.

The restraint assembly 10 additionally includes an adapter buckle 14. The adapter buckle 14 includes an exterior section 24 which in use is disposed proximate to the front 16 of the mounting plate 12. Likewise during use, the interior section 26 is disposed proximate to the rear 18 of the mounting plate 12 within the opening 54. The adapter buckle 14 is coupled to the mounting plate 12 during use of the restraint assembly 10.

In at least one embodiment, the exterior section 24 includes a rectangular head 28. It should be noted that any desired shape may be selected for the head 28 dependent on the requirements of a particular application. The head 28 is integral to an arm 30. The arm 30 descends from the central section of the lower edge of the head 28. The head 28 and arm 30 are preferably integral with each other and are formed of a single portion of stainless steel material.

The head 28 includes a horizontal slot 46 which is centrally positioned and oriented horizontally within the interior of the head 28. The horizontal slot 46 is generally used to releasably receive straps of a patient restraint device. Generally, at least one strap of the patient restraint device is looped through the horizontal slot 46. The at least one strap of the patient restraint device may then be secured to the strap or to an adjustable restraint buckle for tightening or loosening to provide a desired tension relative to the medical bed.

It should be noted that the restraint assembly 10, mounting plate 12, and the adapter buckle 14 function as an anchor on a medical bed during use of a patient restraint device.

In at least one embodiment, the arm 30 extends from the head 28 to the stop 34 which may be "T" shaped. The arm 30, and head 28 as well as the stop 34 are preferably formed of a single piece of stainless steel material.

The arm 30 as previously identified extends outwardly and downwardly from the central portion of the lower edge of the head 28. The arm 30 also extends upwardly from the central portion of the upper edge of the stop 34.

In at least one embodiment, the arm 30 at the approximate midpoint between the head 28 and the stop 34 includes an angular bend 32. The angular bend 32 is approximately 145° creating an angle between the head 28 and the stop 34 of approximately 145° or 35° upwardly from a horizontal plane relative to the stop 34.

In at least one embodiment, the angular bend 32 is the dividing area of the adapter buckle 14 between the exterior section 24 and the interior section 26. The portion of the adapter buckle 14 between the angular bend 32 and the head 28 is the exterior section 24. The portion of the adapter buckle 14 between the angular bend 32 and stop 34 is the interior section 26.

In one embodiment, one or more openings 54 have been placed within a medical bed frame at desired locations. The mounting plates 12 are then secured to the frame of the medical bed as earlier described, where the rear 18 of the mounting plate 12 is centrally positioned over the openings 54.

Any desired number of adapter buckles 14 may then be coupled to any desired number of mounting plates 12 on the medical bed frame. In some embodiments, an adapter buckle 14 will remain coupled to a mounting plate 12 during periods of nonuse. In this embodiment, a strap of a medical device will be looped through a pre-connected horizontal slot 46 of the adapter buckle 14 to enable adjustable tensioning of a patient restraint device.

In at least one alternative embodiment, the horizontal slot 46 of the adapter buckle 14 may be initially engaged to the strap of a patient restraint device, where the adapter buckle 14 may be coupled to the mounting plate 12 immediately prior to the adjustment of the tension to be placed onto the patient restraint device.

In one embodiment, the adapter buckle 14 may be coupled to the mounting plate 12 by the insertion of the stop 34 through the vertical slot 20, and the rotation of the head 28, arm 30, and stop 34 approximately 90°, where the angular bend 32 is used to position the head 28 upwardly proximate to the upper edge 36 and front 16 of the mounting plate 12. In this position, the exterior section 24 including the head 28 is exterior to the vertical slot 20. The interior section 26 including the stop 34 is interior to the vertical slot 20. The stop 34 is positioned proximate to the rear 18 and proximate to the vertical slot 20 within the opening 54.

The size dimensions selected for the stop 34 are required to be less than the height dimension selected for the vertical slot 20, in order for coupling of the adapter buckle 14 and mounting plate 12 to occur.

In one embodiment, the stop 34, prior to positioning through the vertical slot 20, may be turned 90° where the stop 34 is in a vertical orientation as opposed to a horizontal operational orientation which occurs following coupling. When the stop 34 is in the pre-coupled vertical orientation, one end 56 of the "T" may be inserted into the vertical slot 20. Depending on which end 56 of the stop 34 has been inserted into the vertical slot 20, the arm 30 may be lowered or raised until the arm 30 contacts either the upper or lower terminus of the vertical slot 20. The opposite end 56 of the stop 34 may then be either raised or lowered depending upon the location of the arm 30 relative to the vertical slot 20, so that the opposite end 56 of the "T" of the stop 34 is rotated inwardly through the vertical slot 20, positioning both ends 56 to the rear 18 of the mounting plate 12. In this position a portion of the arm 30 and both ends 56 of the stop 34 will be proximate to the rear 18 of the mounting plate 12 within the opening 54. Also a portion of the arm 30 and the head 28 will be proximate to the front 16 of the mounting plate 12. In this second pre-coupled position, the angular bend 32 will be facing to the either of the left or to the right as an individual faces the restraint assembly 10.

In the embodiment where the angular bend 32 is proximate to the left relative to the mounting plate 12, the head 28 may be rotated from a relative position of 270° (or facing horizontally to the left) upwardly 90°, to the final 0° or 360° position. In this coupled position the head 28 is positioned upwardly relative to the vertical slot 20 and is proximate to the upper edge 36 of the mounting plate 12. In this embodiment the stop 34 proximate to the rear 18 of the vertical slot 20 has been rotated to a substantially horizontal position where each of the ends 56 of the stop 34 extends normally and outwardly relative to the vertical slot 20. The extension of the ends 56 of the stop 34 outwardly relative to the vertical slot 20 prohibits the adapter buckle 14 from being pulled forwardly or outwardly away from the opening 54 and through the mounting plate 12. The ends 56 function as anchors or stops prohibiting the separation of the adapter buckle 14 from the mounting plate 12 following coupling.

In an alternative embodiment, where the angular bend 32 is positioned to the right relative to the mounting plate 12, the head 28 may be rotated from a relative position of 90° (or facing horizontally to the right) upwardly 90° to the left, to a final 0° or three 360° upward position. In this embodiment, the head 28 is disposed upwardly relative to the vertical slot 20 and is proximate to the upper edge 36 of the mounting plate 12. In this orientation, the stop 34 proximate to the rear 18 of the vertical slot 20 has been rotated to a substantially horizontal position where each of the ends 56 of the stop 34 extend normally and outwardly relative to the vertical slot 20. The extension of the ends 56 of the stop 34 outwardly relative to the vertical slot 20 prohibit the adapter buckle 14 from being pulled forwardly or outwardly away from the opening 54 and through the mounting plate 12. The ends 56 function as anchors or stops prohibiting the separation of the adapter buckle 14 from the mounting plate 12 following coupling.

In an at rest position the head 28 may be adjacent to the front 16 and upper edge 36, where the restraint assembly 10 is in a substantially flat position relative to a surface. In addition, in the at rest position, the interior section 26, including the arm 30 and the ends 56 of the stop 34 extend rearwardly relative to the vertical slot 20 and downwardly at an approximate angle of 145° downwardly from vertical within the opening 54. In order to initiate use of the restraint assembly 10, the head 28 is moved downwardly and outwardly relative to the front 16 of the mounting plate 12.

In an operational, tensioned position, the head 28 and horizontal slot 46 will be lowered to an angle of approximately 35° downwardly from a vertical position away from the mounting plate 12. In the operational position, the ends 56, stop 34 and interior section 26 of the adapter buckle 14 will be disposed in a substantially normal and horizontal position relative to the vertical mounting plate 12 within the opening 54. The head 28 and horizontal slot 46 will be positioned outwardly relative to the front 16 of the mounting plate 12, so long as a strap of a patient restraint device is engaged to the horizontal slot 46 of the head 28.

In at least one alternative embodiment, the mounting plate 12 may include a lock opening 22 disposed below the vertical slot 20 providing access to the rear 18 and into the opening 54. In this embodiment, the lock opening 22 is constructed and arranged to receive a lock assembly 40 having a lock cylinder 42 which in turn includes a keeper 44. The keeper 44 is disposed within the opening 54 below the stop 34 and ends 56.

In at least one embodiment, a doughnut shaped lock spacer 62 surrounds the lock cylinder 42 prior to insertion of the lock cylinder 42 into the lock opening 22. The lock spacer 62 may be formed of metal, plastic, or rubber materials at the discretion of an individual. The lock spacer 62 is preferably adjacent to and is in contact with the front 16 of the mounting plate 12. The lock spacer 62 may be used to assist in the positioning of the keeper 44 directly below the stop 34 and arm 30. The lock spacer 62 may also provide a moisture seal preventing the lock cylinder 42 from exposure to moisture, which over time may lead to rust and malfunction of the lock assembly 40.

The lock spacer 62 may include a rounded or angled face as positioned adjacent to a key opening to improve the aesthetic appearance of the lock assembly 40.

In one embodiment, the lock assembly 40 may include a positioning adjuster which may be attached to the lock cylinder 42 following the attachment of the lock spacer 62 adjacent to the key face. The positioning adjuster may then be tightened to secure the lock spacer 62 in a desired position between the lock face and the positioning adjuster immediately prior to the positioning of the lock cylinder 42 within the lock opening 22.

Following insertion of the lock cylinder 42 into the lock opening 22 an individual may use a lock retainer to interface with the lock cylinder 42 to the rear 18 in order to sandwich the mounting plate 12 between the lock spacer 62 and the lock retainer. The use of the lock spacer 62 on the front 16 and lock retainer on the rear 18 may facilitate the exact positioning of the lock cylinder 42 and keeper 44 relative to the stop 34.

The lock assembly 40 may be attached to the mounting plate 12 before or after the coupling of the adapter buckle 14 to the mounting plate 12.

Figure 4:
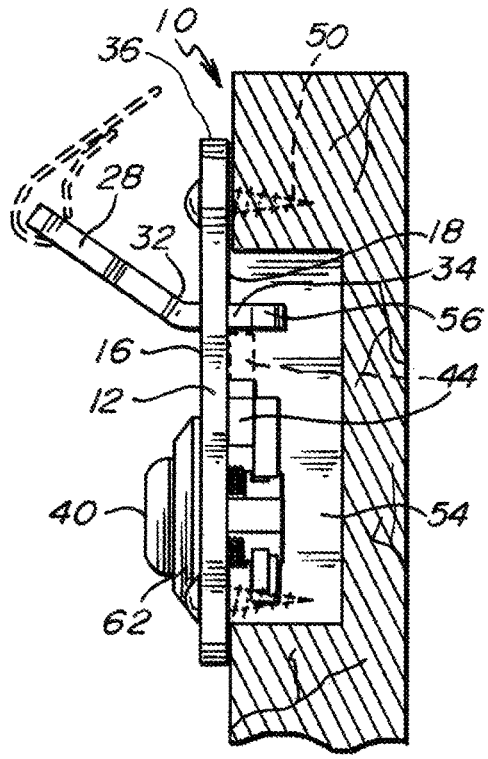
FIG. 4 is a cross-sectional side view of the restraint assembly engaged to a bed taken along the line 4-4 of FIG. 3.
Figure 5:
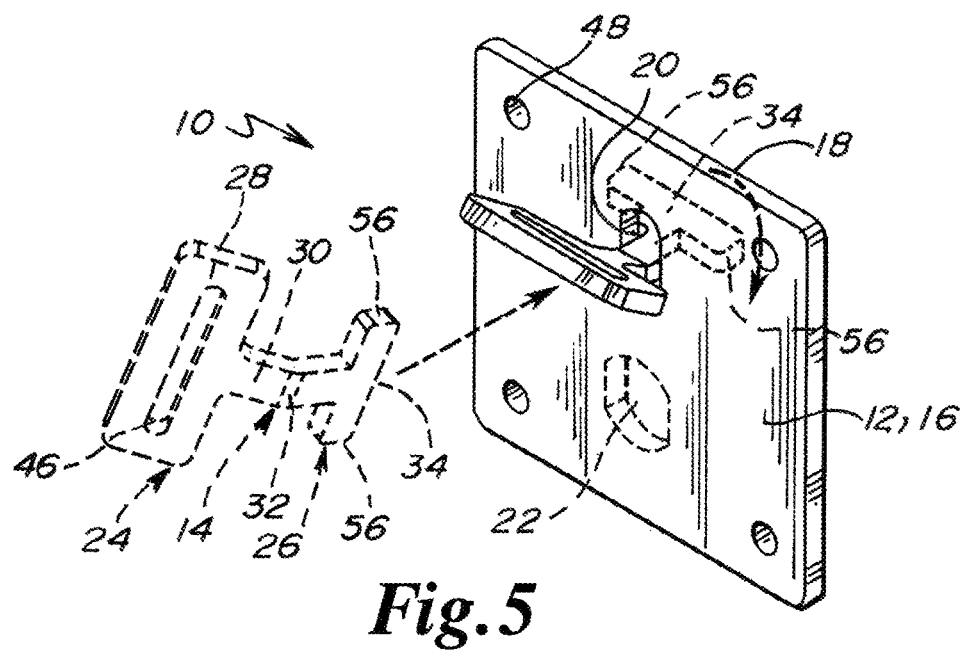
FIG. 5. is a is a perspective phantom-line view of the restraint assembly prior to and following the engagement of the adapter buckle to the mounting plate.

As may be seen in FIG. 4, the lock assembly 40 has an unlocked position and a locked position (shown in phantom line). Referring to FIG. 4, in the unlocked position the keeper 44 has been rotated or positioned horizontally (in either a left or right direction) relative to the vertical slot 20. In the unlocked position the keeper 44 is adjacent to an interior lower edge of the opening 54. In this configuration the interior section 26, including the arm 30, stop 34 and ends 56 may move vertically upwards or downwards within the vertical slot 20. In the unlocked position the movement of the interior section 26 including the arm 30, stop 34 and ends 56 facilitates the ease of connection of a strap of a patient restraint device to the head 28 and horizontal slot 46.

Referring to FIG. 4 in the locked position the keeper 44 has been rotated upwardly approximately 90° to a vertical position. In the locked position the keeper 44 is disposed directly below the arm 30 and stop 34 within the opening 54. In this position, the keeper 44 locks the restraint assembly 10 and does not permit the adapter buckle 14 from being moved in a downward direction within the vertical slot 20. The prevention of movement of the arm 30 and stop 34 downwardly within the vertical slot 20 prohibits the rotation of the ends 56 out of a normal outwardly horizontal position relative to the vertical slot 20. The ends 56 are not permitted to be rotated vertically, and are therefore prohibited from being uncoupled from the mounting plate 12. The rotation of the keeper 44 vertically upward prevents separation of the adapter buckle 14 from the mounting plate 12.

In at least one embodiment the restraint assembly 10 may include a rear cover. The rear cover preferably is rectangular and is formed of metal. The rear cover is also preferably releasably or permanently attached to the rear 18 of the mounting plate 12 in a covering relationship over the arm 30, stop 34, lock cylinder 42 and keeper 44.

In a first embodiment the restraint assembly includes a mounting plate, the mounting plate having a front, a rear, and a vertical slot located centrally with respect to the front, the mounting plate further having a lock opening positioned below the vertical slot; an adapter buckle constructed and arranged for coupling to the mounting plate, the adapter buckle having an exterior section and interior section, the exterior section having a head having a horizontal slot and an arm extending downwardly from the head, the arm having an angular bend, the angular bend having an angle of 145°, the interior section having a portion of the arm below the angular bend, and a "T" shaped stop integral to the arm opposite to the head; wherein the stop is placed in a first pre-coupled position where the stop is in a vertical orientation, the stop being inserted through the vertical slot in a second pre-coupled position, and the exterior section and the interior section being rotated 90° to position the angular bend upwardly and to dispose the head proximate to an upper edge of the mounting plate in the coupled position, wherein the stop extends horizontally outwardly in opposite directions relative to the vertical slot to the rear; and a lock assembly having a lock cylinder and a keeper, the lock cylinder being disposed through the lock opening positioning the keeper to the rear, the keeper having a locked position and an unlocked position wherein in the locked position the keeper is in a upward orientation engaging the stop, and in the unlocked position the keeper is in a horizontal orientation disengaged from the stop.

In a second alternative embodiment according to the first embodiment, the mounting plate has a plurality of apertures, each of the apertures receiving a fastener.

In a third alternative embodiment according to the second embodiment, the mounting plate has a mounting plate shape, the mounting plate shape being selected from the group essentially consisting of rectangular, square, circular, oval, pentagonal, hexagonal and octagonal.

In a fourth alternative embodiment according to the second embodiment, the fasteners are nuts and bolts.

In a fifth alternative embodiment according to the fourth embodiment, the mounting plate and the adapter buckle are formed of stainless steel.

In a sixth alternative embodiment according to the fifth embodiment, the restraint assembly further comprising a rear cover, the rear cover being disposed over the stop and engaged to the rear.

In a seventh alternative embodiment according to the sixth embodiment, the rear cover has a rear cover shape, the rear cover shape being square or rectangular.

In an eighth alternative embodiment according to the seventh embodiment, the head is adjacent to the front of the mounting plate in the coupled position.

In a ninth alternative embodiment according to the eighth embodiment, the head and the horizontal slot are constructed and arranged to receive a restraint strap.

In a tenth alternative embodiment according to the ninth embodiment, the mounting plate has a height dimension of four inches, a width dimension of four inches, and a thickness dimension of $3/16$ inches, the vertical slot has a height dimension of one inch and a width dimension of $1/2$ inch and the rear cover is formed of metal, the rear cover having a height dimension of $1½$ inches, a width dimension of 2 inches, and a depth dimension of 1 inch.

In an eleventh alternative embodiment according to the tenth embodiment, the rear cover is affixed to the rear of the mounting plate by cover fasteners or welding.

In a twelfth alternative embodiment a restraint assembly comprises a mounting plate, the mounting plate having a front, a rear, and a vertical slot located centrally with respect to the front; an adapter buckle is constructed and arranged for coupling to the mounting plate, the adapter buckle having an exterior section and interior section, the exterior section having a head having a horizontal slot and an arm extending downwardly from the head, the arm having an angular bend, the angular bend having an angle of 145°, the interior section having a portion of the arm below the angular bend, and a "T" shaped stop integral to the arm opposite to the head; wherein the stop is placed in a first pre-coupled position where the stop is in a vertical orientation, the stop being inserted through the vertical slot in a second pre-coupled position, and the exterior section and the interior section being rotated 90° to position the angular bend upwardly and to dispose the head proximate to an upper edge of the mounting plate in the coupled position, wherein the stop extends horizontally outwardly in opposite directions relative to the vertical slot to the rear.

In a thirteenth alternative embodiment according to the twelfth embodiment, the mounting plate has a lock opening positioned below the vertical slot and a lock assembly having a lock cylinder and a keeper, the lock cylinder being disposed through the lock opening positioning the keeper to the rear, the keeper having a locked position and an unlocked position wherein in the locked position the keeper is in a upward orientation engaging the stop, and in the unlocked position the keeper is in a horizontal orientation disengaged from the stop.

In a fourteenth alternative embodiment according to the thirteenth embodiment, the mounting plate has a mounting plate shape, the mounting plate shape being selected from the group essentially consisting of rectangular, square, circular, oval, pentagonal, hexagonal and octagonal, the mounting plate and the adapter buckle being formed of stainless steel.

In a fifteenth alternative embodiment according to the fourteenth embodiment, the restraint assembly further comprising a rear cover, the rear cover being disposed over the stop and engaged to the rear.

In a sixteenth alternative embodiment according to the fifteenth embodiment, the mounting plate has a height dimension of four inches, a width dimension of four inches, and a thickness dimension of 3/16 inches, the vertical slot has a height dimension of one inch and a width dimension of ½ inch, and the rear cover is formed of metal, the rear cover having a height dimension of 1½ inches, a width dimension of 2 inches, and a depth dimension of 1 inch.

In a seventeenth alternative embodiment according to the sixteenth embodiment, the rear cover is affixed to the rear of the mounting plate by cover fasteners.

This completes the description of the preferred and alternate embodiments of the invention. Those skilled in the art may recognize other equivalents to the specific embodiment described herein which equivalents are intended to be encompassed by the claims attached hereto.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described embodiments of the invention.

I claim:

1. A restraint assembly comprising:
   a mounting plate, said mounting plate having a front, a rear, and a vertical slot located centrally with respect to said front, said mounting plate further having a lock opening positioned below said vertical slot;
   an adapter buckle constructed and arranged for coupling to said mounting plate, said adapter buckle having an exterior section and interior section, said exterior section having a head having a horizontal slot and an arm extending downwardly from said head, said arm having an angular bend, said angular bend having an angle of 145°, said interior section having a portion of said arm below said angular bend, and a "T" shaped stop integral to said arm opposite to said head;
   wherein said stop is placed in a first pre-coupled position where said stop is in a vertical orientation, said stop being inserted through said vertical slot in a second pre-coupled position, and said exterior section and said interior section being rotated 90° to position said angular bend upwardly and to dispose said head proximate to an upper edge of said mounting plate in said coupled position, wherein said stop extends horizontally outwardly in opposite directions relative to said vertical slot to said rear; and
   a lock assembly having a lock cylinder and a keeper, said lock cylinder being disposed through said lock opening positioning said keeper to said rear, said keeper having a locked position and an unlocked position wherein in said locked position said keeper is in a upward orientation engaging said stop, and in said unlocked position said keeper is in a horizontal orientation disengaged from said stop.

2. The restraint assembly according to claim 1, said mounting plate having a plurality of apertures, each of said apertures receiving a fastener.

3. The restraint assembly according to claim 2, wherein said mounting plate has a mounting plate shape, said mounting plate shape being selected from the group essentially consisting of rectangular, square, circular, oval, pentagonal, hexagonal and octagonal.

4. The restraint assembly according to claim 3, wherein said fasteners are nuts and bolts.

5. The restraint assembly according to claim 4, wherein said mounting plate and said adapter buckle are formed of stainless steel.

6. The restraint assembly according to claim 5, the restraint assembly further comprising a rear cover, said rear cover being disposed over said stop and engaged to said rear.

7. The restraint assembly according to claim 6, said rear cover having a rear cover shape, said rear cover shape being square or rectangular.

8. The restraint assembly according to claim 7, said head being adjacent to said front of said mounting plate in said coupled position.

9. The restraint assembly according to claim 8, said head and said horizontal slot being constructed and arranged to receive a restraint strap.

10. The restraint assembly according to claim 9, wherein said mounting plate has a height dimension of four inches, a width dimension of four inches, and a thickness dimension of 3/16 inches.

11. The restraint assembly according to claim 10, wherein said vertical slot has a height dimension of one inch and a width dimension of ½ inch.

12. The restraint assembly according to claim 11, wherein said rear cover is formed of metal, said rear cover having a height dimension of 1½ inches, a width dimension of 2 inches, and a depth dimension of 1 inch.

13. The restraint assembly according to claim 12, wherein said rear cover is affixed to said rear of said mounting plate by cover fasteners.

\* \* \* \* \*